(12) United States Patent
Karim et al.

(10) Patent No.: US 7,811,486 B2
(45) Date of Patent: Oct. 12, 2010

(54) METHOD OF MANUFACTURING A HARDENABLE DENTAL ARTICLE

(75) Inventors: Naimul Karim, Maplewood, MN (US); Darin J. Meyertholen, Woodbury, MN (US); Robert M. Biegler, Woodbury, MN (US); Kevin M. Cummings, Little Canada, MN (US); Lance C. Gore, River Falls, WI (US); James R. Kvitrud, White Bear Lake, MN (US); Robert W. Peterson, Spring Valley, WI (US); Daniel T. Scott, Huntington Beach, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 1118 days.

(21) Appl. No.: 10/921,648

(22) Filed: Aug. 19, 2004

(65) Prior Publication Data

US 2005/0100868 A1 May 12, 2005

Related U.S. Application Data

(63) Continuation-in-part of application No. 10/643,749, filed on Aug. 19, 2003, now abandoned.

(51) Int. Cl.
*B29C 43/02* (2006.01)
(52) U.S. Cl. .......................... 264/17; 264/19; 264/313; 264/320
(58) Field of Classification Search ........................ None
See application file for complete search history.

(56) References Cited

U.S. PATENT DOCUMENTS

| | | | |
|---|---|---|---|
| 622,068 A * | 3/1899 | Payne ............................ 72/61 |
| 1,468,428 A | 9/1923 | Wells et al. | |
| 1,864,365 A * | 6/1932 | Montgomery ................. 264/86 |
| 1,896,123 A | 2/1933 | Schweitzer | |

(Continued)

FOREIGN PATENT DOCUMENTS

DE  2751057 A1  6/1981

(Continued)

OTHER PUBLICATIONS

ANSI/ADA, American National Standard/American Dental Association, Specification No. 27; "Resin-Based Filling Material;" Council on Dental Materials, Instruments and Equipment, American Dental Association; Chicago, IL; 36 pgs. total (Jul. 16, 1993).

(Continued)

*Primary Examiner*—Edmund H. Lee
(74) *Attorney, Agent, or Firm*—Carolyn A. Fischer

(57) ABSTRACT

Methods of manufacturing hardenable dental articles, packaged hardenable dental articles, and methods of packaging hardenable dental articles are disclosed. In various embodiments, the manufacturing may involve molding a hardenable dental material in a mold cavity that may be lined with a mold liner. The mold body may also form the package of the hardenable dental article formed within the mold cavity. In other embodiments, the hardenable dental articles may be provided in mold cavities located in sacrificial mold bodies that may be torn, stretched, softened, dissolved, etc. to release the hardenable dental articles in the mold cavities.

26 Claims, 8 Drawing Sheets

U.S. PATENT DOCUMENTS

| | | | |
|---|---|---|---|
| 2,271,454 A * | 1/1942 | Erdle et al. | 264/227 |
| 2,310,448 A * | 2/1943 | Leib | 433/39 |
| 2,332,537 A * | 10/1943 | Slatis | 264/20 |
| 2,474,676 A * | 6/1949 | Kelly | 264/20 |
| 2,480,048 A | 8/1949 | Rice | |
| 2,551,812 A * | 5/1951 | Nelson | 156/61 |
| 2,678,470 A * | 5/1954 | Slack, Jr. | 264/20 |
| 3,390,458 A | 7/1968 | Lytton | |
| 3,565,387 A | 2/1971 | Neustadter et al. | |
| 3,585,723 A | 6/1971 | Simor | |
| 3,949,476 A | 4/1976 | Kahn | |
| 3,997,637 A * | 12/1976 | Rogers | 264/19 |
| 4,071,424 A | 1/1978 | Dart et al. | |
| 4,080,412 A * | 3/1978 | Colpitts et al. | 264/17 |
| 4,113,499 A | 9/1978 | Ivanov et al. | |
| 4,115,488 A * | 9/1978 | Colpitts | 264/17 |
| 4,129,946 A | 12/1978 | Kennedy | |
| 4,278,630 A * | 7/1981 | Scheicher | 264/122 |
| 4,347,888 A | 9/1982 | Butler | |
| 4,431,420 A | 2/1984 | Adair | |
| 4,449,936 A | 5/1984 | Bayer | |
| 4,503,169 A | 3/1985 | Randklev | |
| 4,507,466 A | 3/1985 | Tomalia et al. | |
| 4,514,174 A | 4/1985 | Dougherty et al. | |
| 4,558,120 A | 12/1985 | Tomalia et al. | |
| 4,568,737 A | 2/1986 | Tomalia et al. | |
| 4,571,188 A | 2/1986 | Hamilton | |
| 4,585,417 A * | 4/1986 | Sozio et al. | 433/202.1 |
| 4,587,329 A | 5/1986 | Tomalia et al. | |
| 4,631,337 A | 12/1986 | Tomalia et al. | |
| 4,642,126 A | 2/1987 | Zador et al. | |
| 4,648,843 A | 3/1987 | Mitra | |
| 4,652,274 A | 3/1987 | Boettcher et al. | |
| 4,694,064 A | 9/1987 | Tomalia et al. | |
| 4,695,251 A | 9/1987 | Randklev | |
| 4,713,975 A | 12/1987 | Tomalia et al. | |
| 4,718,849 A | 1/1988 | Weissenfluh et al. | |
| 4,737,550 A | 4/1988 | Tomalia | |
| 4,767,331 A * | 8/1988 | Hoe | 433/213 |
| 4,772,530 A | 9/1988 | Gottschalk et al. | |
| 4,776,795 A * | 10/1988 | Hornig | 433/223 |
| 4,778,386 A | 10/1988 | Spiry | |
| 4,857,599 A | 8/1989 | Tomalia et al. | |
| 4,871,779 A | 10/1989 | Killat et al. | |
| 4,874,450 A | 10/1989 | Gottschalk | |
| 4,954,414 A | 9/1990 | Adair et al. | |
| 4,957,441 A | 9/1990 | Bryan | |
| 5,024,790 A * | 6/1991 | Grossman et al. | 264/16 |
| 5,055,372 A | 10/1991 | Shanklin et al. | |
| 5,057,393 A | 10/1991 | Shanklin et al. | |
| 5,066,231 A | 11/1991 | Oxman et al. | |
| 5,102,332 A | 4/1992 | Uthoff | |
| 5,135,545 A | 8/1992 | Pyzik et al. | |
| 5,332,390 A | 7/1994 | Rosellini | |
| 5,401,169 A | 3/1995 | Fleisher et al. | |
| 5,403,188 A | 4/1995 | Oxman et al. | |
| 5,418,301 A | 5/1995 | Hult et al. | |
| 5,487,663 A | 1/1996 | Wilson | |
| 5,538,129 A | 7/1996 | Chester et al. | |
| 5,545,676 A | 8/1996 | Palazzotto et al. | |
| 5,552,177 A | 9/1996 | Jacobs et al. | |
| 5,635,545 A | 6/1997 | Oxman et al. | |
| 5,636,736 A | 6/1997 | Jacobs et al. | |
| 5,707,236 A | 1/1998 | Swanson et al. | |
| 5,753,781 A | 5/1998 | Oxman et al. | |
| 5,775,913 A | 7/1998 | Updyke et al. | |
| 5,785,178 A | 7/1998 | Kvitrud et al. | |
| 5,827,063 A | 10/1998 | Greenstein | |
| 5,830,986 A | 11/1998 | Merrill et al. | |
| D403,768 S | 1/1999 | Mark et al. | |
| 5,859,148 A | 1/1999 | Borggreve et al. | |
| 5,876,209 A | 3/1999 | Letcher | |
| 5,914,185 A | 6/1999 | Shoher et al. | |
| 5,919,870 A | 7/1999 | Letchford et al. | |
| 5,951,294 A | 9/1999 | Pierson | |
| 5,975,906 A | 11/1999 | Knutson | |
| 5,996,796 A | 12/1999 | Kvitrud et al. | |
| 6,057,383 A | 5/2000 | Völkel et al. | |
| 6,084,004 A | 7/2000 | Weinmann et al. | |
| 6,114,409 A | 9/2000 | Krebber | |
| 6,121,344 A | 9/2000 | Angeletakis et al. | |
| 6,126,922 A | 10/2000 | Rozzi et al. | |
| 6,127,450 A | 10/2000 | Angeletakis | |
| 6,183,249 B1 | 2/2001 | Brennan et al. | |
| 6,186,790 B1 | 2/2001 | Karmaker et al. | |
| 6,187,836 B1 | 2/2001 | Oxman et al. | |
| 6,196,840 B1 | 3/2001 | Zentz et al. | |
| 6,244,870 B1 * | 6/2001 | Sakata et al. | 433/213 |
| 6,252,014 B1 | 6/2001 | Knauss | |
| 6,283,755 B1 | 9/2001 | Bergström et al. | 433/193 |
| 6,300,390 B1 | 10/2001 | Angeletakis | |
| 6,345,984 B2 | 2/2002 | Karmaker et al. | |
| 6,353,040 B1 | 3/2002 | Subelka et al. | |
| 6,359,090 B1 | 3/2002 | Angeletakis | |
| 6,382,980 B1 | 5/2002 | Shoher et al. | |
| 6,384,106 B1 | 5/2002 | Angeletakis | |
| 6,395,803 B1 | 5/2002 | Angeletakis | |
| 6,415,916 B1 | 7/2002 | Rini | |
| 6,448,301 B1 | 9/2002 | Gaddam et al. | |
| 6,488,503 B1 * | 12/2002 | Lichkus et al. | 433/202.1 |
| 6,506,816 B1 | 1/2003 | Ario et al. | |
| 6,572,693 B1 | 6/2003 | Wu et al. | |
| 6,592,369 B2 | 7/2003 | Sun et al. | |
| 6,624,211 B2 | 9/2003 | Karim et al. | |
| 6,635,690 B2 | 10/2003 | Heilmann et al. | |
| 6,664,306 B2 | 12/2003 | Gaddam et al. | |
| 6,696,507 B2 | 2/2004 | Subelka et al. | 523/115 |
| 6,790,035 B2 | 9/2004 | Tricca et al. | |
| 6,846,181 B2 | 1/2005 | Karmaker et al. | |
| 6,964,985 B2 | 11/2005 | Karim et al. | |
| 7,114,951 B2 | 10/2006 | Sun et al. | |
| 7,134,875 B2 | 11/2006 | Oxman et al. | |
| 7,175,433 B2 | 2/2007 | Sun et al. | |
| 2002/0061493 A1 | 5/2002 | Sun et al. | |
| 2002/0081546 A1 | 6/2002 | Tricca et al. | |
| 2002/0086266 A1 | 7/2002 | Karmaker et al. | |
| 2002/0102519 A1 | 8/2002 | Baum et al. | |
| 2002/0115743 A1 | 8/2002 | Karim et al. | |
| 2002/0117393 A1 | 8/2002 | Sun et al. | |
| 2003/0096908 A1 | 5/2003 | Heilmann et al. | |
| 2003/0114553 A1 | 6/2003 | Karim et al. | |
| 2003/0134930 A1 | 7/2003 | Gaddam et al. | |
| 2003/0153645 A1 | 8/2003 | Sun et al. | |
| 2003/0203339 A1 | 10/2003 | Chilibeck | |
| 2004/0005277 A1 | 1/2004 | Villison et al. | 424/53 |
| 2004/0005524 A1 | 1/2004 | Oxman et al. | |
| 2004/0082683 A1 | 4/2004 | Karim et al. | |
| 2004/0084792 A1 | 5/2004 | Sun et al. | |
| 2004/0224283 A1 | 11/2004 | Sun et al. | |
| 2005/0040551 A1 | 2/2005 | Biegler et al. | |
| 2005/0042576 A1 | 2/2005 | Oxman et al. | |
| 2005/0042577 A1 | 2/2005 | Kvitrud et al. | |
| 2005/0147944 A1 | 7/2005 | Karim et al. | |
| 2006/0119003 A1 | 6/2006 | Karim et al. | |
| 2007/0018346 A1 | 1/2007 | Sun et al. | |

FOREIGN PATENT DOCUMENTS

| | | |
|---|---|---|
| DE | 299 21 182 U1 | 5/2000 |
| DE | 199 24 116 A1 | 1/2001 |
| EP | 0 173 567 A2 | 3/1986 |
| EP | 0 284 991 A2 | 10/1988 |
| EP | 0 284 991 A3 | 10/1988 |
| EP | 0 284 991 B1 | 8/1992 |

| EP | 0 970 680 A2 | 1/2000 |
|---|---|---|
| EP | 0 970 680 A3 | 1/2000 |
| EP | 1 138 272 A1 | 10/2001 |
| FR | 2455795 | 11/1980 |
| FR | 2598076 | 11/1987 |
| GB | 647 261 | 12/1950 |
| GB | 1 051 735 | 12/1966 |
| GB | 1 591 741 | 6/1981 |
| JP | 4-183737 | 6/1992 |
| JP | 4-357948 | 12/1992 |
| JP | 2003-147328 | 5/2003 |
| WO | WO 95/35071 | 12/1995 |
| WO | WO 98/35630 A2 | 8/1998 |
| WO | WO 98/35630 A3 | 8/1998 |
| WO | WO 98/36729 A2 | 8/1998 |
| WO | WO 99/45890 A1 | 9/1999 |
| WO | WO 01/12679 A1 | 2/2001 |
| WO | WO 01/95862 A1 | 12/2001 |
| WO | WO 02/26197 A2 | 4/2002 |
| WO | WO 02/26197 A3 | 4/2002 |
| WO | WO 02/36039 A1 | 5/2002 |
| WO | WO 02/085313 A1 | 10/2002 |
| WO | WO 02/092021 A1 | 11/2002 |
| WO | WO 03/015720 A1 | 2/2003 |
| WO | WO 03/082142 | 10/2003 |
| WO | WO 2006/119003 | 11/2006 |
| WO | WO 2007/078006 | 4/2007 |
| WO | WO 2007/078235 | 4/2007 |
| WO | WO 2007/078257 | 4/2007 |

OTHER PUBLICATIONS

Fedors, "A Method for Estimating Both the Solubility Parameters and Molar Volumes of Liquids," *Polymer Eng. and Sci.*, vol. 14(2), pp. 147-154 (Feb. 1974).

ISO 4049 International Standard; "Dentistry—Polymer-based filling, restorative and luting materials;" International Organization for Standardization, Geneva, Switzerland; Title page, Publication page, Table of Contents, and pp. 1-27 (33 pgs. total) (Jul. 15, 2000).

Klee et al., "Monomers for low shrinking composites, $2^a$ Synthesis of branched methacrylates and their application in dental composites," *Macromol. Chem. Phys.*, vol. 200, pp. 517-523 (1999).

Plate et al., "Comb-Like Polymers, Structure and Properties," *Journal of Polymer Science, Macromolecular Reviews*, vol. 8, Title page, Publication and Table of Contents page, and pp. 117-253 (1974).

Product Directions for Use and Material Safety Data Sheet, Triad® Visible-Light Cure Provisional Material Directions for Use, Dentsply Trubyte, York, PA, 6 pgs. (Jun. 1997).

Product Directions for Use, SureFil™ High Density Posterior Restorative, Dentsply Caulk, Dentsply, International, Inc., Milford, DE, 5 pgs. (Oct. 1998).

Product Directions for Use, REVOTEK LC Light-Cured Resin for Temporary Crown & Bridge, GC Dental Products Corp., Alslo, IL, 5 pgs. (Nov. 2000).

Product Instructions for Use, Kerr Prodigy Condensable, Kerr U.S.A., Orange, CA, 1 pg. (no date available).

Revised American National Standard/American Dental Association (ADA); Specification No. 9 for Dental Silicate Cement; ADA, Chicago, IL; 17 pgs. (Jun. 30, 1980).

Wan et al., "Methacrylol Derivitized Hyperbranched Polyester. 2. Photo-Polymerization and Properties for Dental Resin Systems," *J.M. S.—Pure Appl. Chem.*, vol. A37(11), pp. 1317-1331 (2000).

"Radica provisona & diagnostic resin" datasheet [online]. DENTSPLY Ceramico, Burlington, NJ, [retrieved on Aug. 17, 2007]. Retrieved from the Internet: <URL:http://www.ceramco.com/prod_radica.shtml>; 2 pgs.

Lichkus, J., "Comparative DSC Study of Novel Composite Radica, Cristobal + and Esthet-X," the IADR/AADR/CADR 85th General Session and Exhibition [online]. New Orleans, LA, Mar. 21-24, 2007 available online [retrieved on Aug. 24, 2007] Retrieved from the Internet: <URL:http://iadr.confex.com/iadr/2007orleans/techprogram/abstract_90574.htm>; 1pg.

"REVOTEK LC Light-gured Composite Resin for Temporary Restorations" datasheet [online]. GC America Inc., Alsip, IL, [retrieved on Aug. 28, 2007]. Retrieved from the Internet: <URL:http://www.gcamerica.com>; 2 pgs.

* cited by examiner

METHOD OF MANUFACTURING A HARDENABLE DENTAL ARTICLE

RELATED APPLICATIONS

This application is a continuation-in-part of U.S. patent application Ser. No. 10/643,749, titled HARDENABLE DENTAL ARTICLE AND METHOD OF MANUFACTURING THE SAME, filed on Aug. 19, 2003 now abandoned, which is incorporated herein by reference in its entirety.

BACKGROUND

Restorative dentistry is an important market in today's dental industry. In particular, tooth repair with temporary and permanent crowns is a common procedure, typically requiring multiple dental appointments. Conventional technologies use liners, adhesives, pastes, two-part powder/liquid systems, preformed metal temporary crowns, and ceramic or porcelain/metal permanent crowns.

Among the problems associated with the conventional technologies are the need for multiple visits to a dentist if a customized dental article is desired. Conversely, if customization is not desired, the dental article used may have a less than desirable fit and/or appearance, e.g., a metallic finish, larger gaps between proximal teeth, significant color variations from natural teeth, etc.

Hardenable dental materials have been developed to address some of these issues. Examples of some of these materials are described in, e.g., International Publication No. WO 03/015720 (Karim et al.) and U.S. application Ser. No. 10/219,398 filed Aug. 15, 2002 (Karim et al.), both titled HARDENABLE SELF-SUPPORTING STRUCTURES AND METHODS. For the purposes of the present invention, "hardenable dental materials" are materials that are capable of being hardened to form dental articles such as crowns, etc.

Although these materials may address the issues identified with respect to conventional technologies, they raise issues of their own with respect to the manufacturing, handling, and packaging of dental articles constructed of such materials. Many of these hardenable dental materials may exhibit significant levels of adhesion during manufacturing. As a result, shaping and handling of the hardenable dental materials into dental articles as a part of the manufacturing process may present challenges.

Another potential issue raised with some hardenable dental materials is that the techniques used to form the hardenable dental materials into usable dental articles may contribute to or detract from the finished appearance of the dental articles. In other words, the hardenable dental material may exhibit an undesirable rough appearance due to less than desirable forming techniques and/or packaging.

In addition, although the exact shape of dental articles manufactured of the hardenable materials before final hardening may be adjusted, significant shaping of the materials may not be possible or desirable depending on the properties of the hardenable dental material being used. For example, the dentist may prefer that the materials be provided in a shape that is close to the final desired shape of the dental article—subject to some minor shaping to provide a more customized fit and/or appearance. By providing the hardenable dental materials in a form that is close to the final form needed by the dentist, the time required for the dentist to complete any given dental procedure in which the dental article is used can be reduced. Such forming, however, may exacerbate the problems identified in the preceding paragraphs.

SUMMARY OF THE INVENTION

The present invention provides methods of manufacturing hardenable dental articles, packaged hardenable dental articles, and methods of packaging hardenable dental articles. In various embodiments, the manufacturing may involve molding a hardenable dental material in a mold cavity that may be lined with a mold liner. The mold body may also form the package of the hardenable dental article formed within the mold cavity. In other embodiments, the hardenable dental articles may be provided in mold cavities located in sacrificial mold bodies that may be torn, stretched, softened, dissolved, etc. to release the hardenable dental articles in the mold cavities.

The use of a mold liner during manufacturing of hardenable dental articles from hardenable dental materials may provide a number of potential advantages such as assisting with release of the hardenable dental article from the mold cavity; protecting the hardenable dental article from contamination, enhancing the finish of the hardenable dental article by providing a smooth finish on the article during the forming process (if the liner itself is smooth), and enhancing the finish of the dental article after hardening (if the smooth inside surface of the mold liner is retained in intimate contact with the outer surfaces of the hardenable dental article during hardening).

If a mold liner, outer liner, or sacrificial mold body having a cavity therein is used in connection with the manufacturing of a hardenable dental article, it may be preferred that the interior surfaces of the cavity in the mold liner, outer liner, or sacrificial mold body conform to substantially all of the outer surfaces of the hardenable dental article after release of the hardenable dental article from the mold cavity. In some instances, it may be preferred that the interior surfaces of the cavity containing the hardenable dental article be in intimate contact with substantially all of the outer surfaces of the hardenable dental article. In the case of dental crown forms, the outer surfaces of the hardenable dental article include those surfaces typically located above the gum line after the dental crowns are located within a subject, e.g., incisal, occlusal, lingual, facial, mesial, buccal, and distal surfaces (as found in any individual dental crown). Alternatively, the hardenable dental article may release from the mold liner after or during its removal from the mold cavity.

If the mold liner is retained on the outer surfaces of the hardenable dental article, various advantages may potentially be obtained. If, for example, the dental article is a crown and the hardenable dental material is a photocurable material, the mold liner may function as an actinic light barrier to retard the passage of actinic radiation that could otherwise prematurely harden the photocurable hardenable dental material. If the liner is malleable, the dentist may be able to customize or adjust the shape of the dental crown with the liner in place. Alternatively, the dentist may remove the liner before customizing.

The liner may also function as a protective barrier for the outer surfaces of the hardenable dental article. If the liner is maintained in place on the outer surfaces of the hardenable dental article during hardening, it may protect the outer surfaces from, e.g., exposure to oxygen before and during the hardening process. If the liner is to be retained in place during hardening, the liner may be flexible to allow the dentist to customize or shape the hardenable dental article before hardening (if desired).

By retaining the liner in place on the outer surfaces of the hardenable dental articles, the liner may also function as a portion of the packaging of the hardenable dental articles manufactured of hardenable dental materials in accordance with the present invention. For example, the liner (in intimate contact with the outer surfaces of the hardenable dental article) may function as a package cover while a package base is attached to contain the hardenable dental article therein (in a manner similar to a "blister pack").

Although mold cavities formed in reusable mold bodies made of conventional materials such as metals, etc. may be used in connection with manufacturing of hardenable dental articles of the present invention, the present invention may also include the use of mold cavities located in sacrificial mold bodies that include, e.g., lines of weakness formed therein, such that after molding or forming of the hardenable dental material into the shape of the selected hardenable dental article, the sacrificial mold body can be separated along the lines of weakness to remove the hardenable dental article from the mold cavity. Other sacrificial mold bodies may be manufactured of materials that can either be stretched or torn to remove the hardenable dental article in the absence of defined lines of weakness. Still other sacrificial mold bodies may be manufactured of materials that can be softened or dissolved by contact with a solvent (such as, e.g., water) that does not significantly adversely affect the hardenable dental article. For example, sacrificial mold bodies could be manufactured of water-soluble materials such that exposure to water (by, e.g., sprays, baths, etc.) softens or dissolves the sacrificial mold body such that the hardenable dental article can be removed—preferably without distorting the shape of the hardenable dental article. All of such mold bodies are described as "sacrificial" because they cannot be reused due to their destruction during the removal process.

Removal of a hardenable dental article from a sacrificial mold body may be performed as part of the manufacturing process, with the shaped hardenable dental article being packaged for delivery to a customer after the hardenable dental article has been removed from the sacrificial mold cavity. Alternatively, the sacrificial mold body itself may form a part of the packaging of the hardenable dental article located therein, with removal of the hardenable dental article from the sacrificial mold cavity being performed by, e.g., the dentist or an assistant, at the point of use of the hardenable dental articles. Such sacrificial mold bodies may be used in connection with mold liners as well.

As used herein, the term "dental article" includes, but is not limited to, dental restoratives and dental prostheses, including, e.g., temporary, intermediate, and permanent crowns and bridges, inlays, onlays, implants, dentures, and artificial teeth, etc., as well as orthodontic appliances (e.g., retainers, night guards, etc.), tooth facsimiles or splints, maxillofacial prostheses, and other customized structures.

As used herein, a "hardenable dental article" may optionally be defined as a self-supporting structure of a hardenable dental material that is dimensionally stable and will maintain its shape (e.g., the preformed shape of a dental crown) without significant deformation at room temperature (i.e., about 20° C. to about 25° C.) for at least two weeks when free-standing (i.e., without any external support). Preferably, the hardenable dental articles of the present invention are dimensionally stable at room temperature for at least about one month, and, more preferably, for at least about six months. Also, it may be preferred that the hardenable dental articles of the present invention are dimensionally stable at temperatures above room temperature, more preferably up to about 40° C., even more preferably up to about 50° C., and even more preferably up to about 60° C. This definition applies in the absence of conditions or materials that would otherwise act to harden the hardenable dental article and in the absence of an external force other than gravity.

In one aspect, the present invention provides a method of manufacturing a hardenable dental article by providing a mold cavity in a shape of a hardenable dental article, wherein the mold cavity has an opening; forcing a hardenable dental material into the mold cavity through the opening; providing an outer liner between the hardenable dental material and the mold cavity; and removing the hardenable dental material and the outer liner from the mold cavity, wherein the hardenable dental material has the shape of the hardenable dental article.

In another aspect, the present invention provides a packaged hardenable dental article including a mass of hardenable dental material in the shape of a hardenable dental article, wherein the hardenable dental article has a base and outer surfaces extending from the base; a package cover conforming to substantially all of the outer surfaces of the hardenable dental article, wherein the package cover includes a polymeric film plastically deformed by the mass of hardenable dental material; and a package base facing the base of the hardenable dental article; wherein the package cover and the package base are attached together about a periphery of the base of the hardenable dental article such that the hardenable dental article is contained within the package base and the package cover.

In another aspect, the present invention provides a dental article that includes a sacrificial mold body with a sacrificial mold cavity in the shape of a hardenable dental article, wherein the sacrificial mold body includes at least one line of weakness formed therein; and a mass of hardenable dental material located within the volume of the sacrificial mold cavity such that the hardenable dental material is in the shape of the hardenable dental article.

In another aspect, the present invention provides a packaged hardenable dental article that includes a mass of hardenable dental material in the shape of a hardenable dental article, wherein the hardenable dental article has a base and outer surfaces extending from the base; a package cover conforming to substantially all of the outer surfaces of the hardenable dental article, wherein the package cover includes a sacrificial mold body with a sacrificial mold cavity in the shape of the hardenable dental article, an opening into the sacrificial mold cavity, and wherein the sacrificial mold body includes at least one line of weakness formed therein; and a package base covering the opening into the sacrificial mold cavity and facing the base of the hardenable dental article; wherein the package cover and the package base are attached together about a periphery of the base of the hardenable dental article such that the hardenable dental article is contained within the package base and the package cover.

In another aspect, the present invention provides a dental article that includes a sacrificial mold body with a sacrificial mold cavity in a shape of a hardenable dental article, wherein the sacrificial mold cavity conforms to substantially all of the outer surfaces of the hardenable dental article, and wherein the sacrificial mold body comprises a water soluble polymer; and a mass of hardenable dental material located within the volume of the sacrificial mold cavity such that the hardenable dental material is in the shape of the hardenable dental article.

In another aspect, the present invention provides a method of manufacturing a hardenable dental article by providing a sacrificial mold body with a sacrificial mold cavity in a shape of a hardenable dental article and an opening into the sacrificial mold cavity, wherein the sacrificial mold body includes a water soluble polymer; and forcing a hardenable dental material into the sacrificial mold cavity through the opening, wherein the hardenable dental material takes the shape of the hardenable dental article.

In another aspect, the present invention provides a method of manufacturing a hardenable dental article by providing a sacrificial mold body with a sacrificial mold cavity in a shape of the hardenable dental article, wherein the sacrificial mold cavity has an opening, and wherein the sacrificial mold body includes at least one line of weakness formed therein; and forcing a hardenable dental material into the sacrificial mold cavity through the opening, wherein the hardenable dental material takes the shape of the hardenable dental article.

These and other features and advantages of the present invention may be described in more detail in connection with various illustrative embodiments of the invention below.

DETAILED DESCRIPTION OF ILLUSTRATIVE EMBODIMENTS OF THE INVENTION

Figure 1:
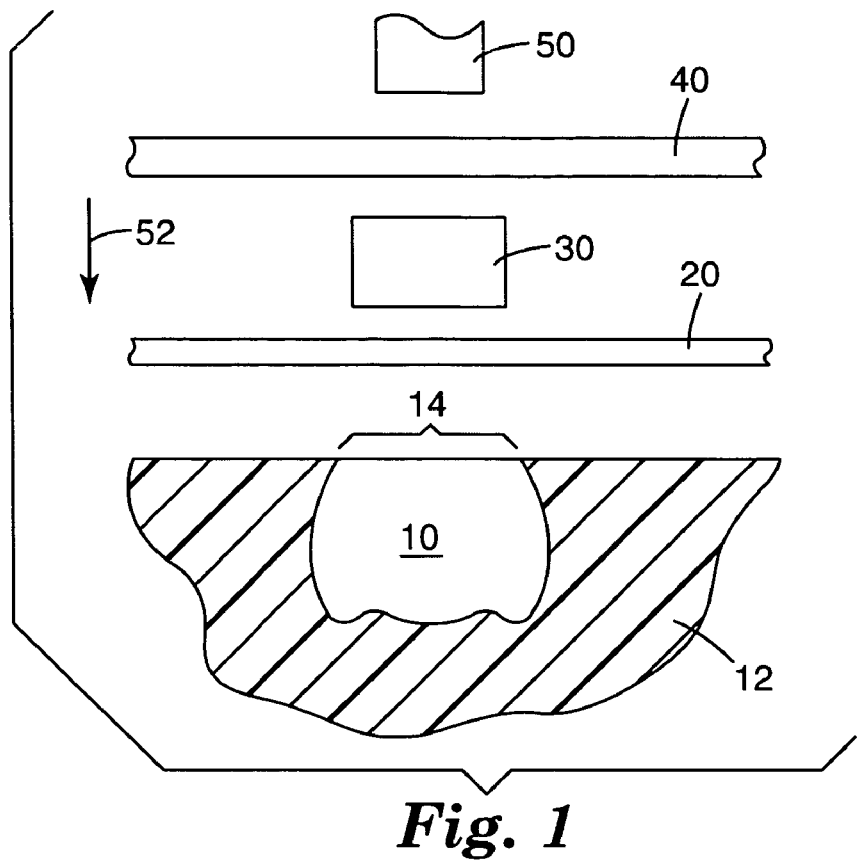
FIG. 1 is an exploded schematic diagram of one illustrative manufacturing process according to the present invention.

In the following detailed description of illustrative embodiments, reference is made to the accompanying figures of the drawing, which form a part hereof, and in which are shown, by way of illustration, specific embodiments in which the invention may be practiced. It is to be understood that other embodiments may be utilized and structural changes may be made without departing from the scope of the present invention.

FIG. 1 is an exploded diagram illustrating one process of forming a hardenable dental article according to the present invention. The illustrated process includes a mold cavity 10 formed in a body 12. The mold cavity 10 includes an opening 14 leading to the volume of the mold cavity itself, which is depicted in cross-section in FIG. 1. In the depicted embodiment, the mold cavity 10 is in the shape of a dental crown. It should, however, be understood that the hardenable dental articles of the present invention may include a wide variety of articles as discussed above.

The mold body 12 may be formed in any suitable material or combination of materials, e.g., metals, polymeric materials, etc. that provide sufficient structural integrity to withstand the forming process as described herein. In some instances, the mold body 12 may be formed in separable sections to facilitate removal of a hardenable dental article formed therein. Also, the mold body 12 may be made of or coated with a material adapted to aid release of a hardenable dental article from the interior surfaces of the mold cavity 10. For example, the interior surfaces of the mold cavity 10 may be coated with, e.g., fluorinated polymers (e.g., PTFE, etc.), boron carbide, chrome, thin dense chrome, chromium nitride, electroless nickel infused with fluorinated polymers, modified tungsten disulfide (e.g., DICRONITE), etc.

In other variations, the mold cavity 10 may be temperature controlled to assist in the molding process by, e.g., heating and/or cooling the temperature of the interior surfaces of the mold cavity 10. In yet other variations, the mold cavity 10 may be vented or evacuated during the molding process to enhance molding. Ultrasonic or other vibrational energy may also be used to enhance filling of the mold cavity 10 and/or assist with release the article from the mold cavity 10.

A mold liner 20 is depicted in FIG. 1 as positioned in between a mass of hardenable dental material 30 and the opening 14 into the mold cavity 10. A pin liner 40 is positioned between the mass of hardenable dental material 30 and a core pin 50. The core pin 50 is preferably used to force the mass of hardenable dental material 30 into the mold cavity 10 through the opening 14 therein. As a result, the core pin 50, a portion of the pin liner 40, the hardenable dental material 30, and a portion of the mold liner 20 are all advanced in the direction of arrow 52 as depicted in FIG. 1. The mold liner 20 functions as an outer liner located between the hardenable dental material 30 and the mold cavity 10.

The mass of hardenable dental material 30 may be preformed into a shape suitable for molding into the desired finished dental article. The hardenable dental material 30 may be provided in the shape of, e.g., a circular cylinder, circular cone, rectangular prism, spherical pellet, etc.

Further, the shape of the core pin 50 may be selected such that it enhances molding of the hardenable dental material 30 within the mold cavity 10. In addition, it may be desirable if the core pin 50 is shaped such that it seals or closes the mold cavity to, e.g., define the edge of the molded hardenable dental article and/or to prevent or reduce the chances of unwanted voids in the hardenable dental material 30 within the mold cavity 10. The shape of the core pin may also be selected to form an interior cavity (see core pine 150 and interior cavity 154 in FIG. 2A) within the hardenable dental article such that a desired shape is imparted to the interior profile of the finished hardenable dental article.

The process illustrated in FIG. 1 may be described as a compression molding process. It should, however, be understood that the hardenable dental material 30 may be formed into the shape of the hardenable dental article by any suitable process. Some suitable processes may include, but are not limited to, e.g., injection molding, forging, casting, vacuum forming, extrusion molding, thermoforming, transfer molding, blow molding, etc.

In the process, the mold liner 20 may be stretched to conform to the shape of the mold cavity 10. At the same time, the mass of hardenable dental material 30 is also molded to conform to the shape of the mold cavity 10. The hardenable dental material 30, will, however, be slightly smaller than the mold cavity 10 because the mold liner 20 is interposed between the hardenable dental material 30 and the interior surfaces of the mold cavity 10.

Stretching of the mold liner 20 may reduce the chances of unwanted voids in the molded hardenable dental article (due to, e.g., wrinkling of the mold liner 20). Furthermore, stretching of the mold liner 20 during the molding process may also enhance intimate contact between the mold liner 20 and the outer surfaces of the molded hardenable dental article.

It should be understood that the mold liner 20 is an optional component in the molding process. In other words, it may be possible to force the hardenable dental material 30 into the mold cavity 10 and remove it therefrom after molding. The mold liner 20 may, however, provide some potential advantages as discussed herein with respect to removal of the hardenable dental material from the mold cavity 10, packaging of the hardenable dental article, etc.

The mold liner 20 may be constructed of a variety of different materials. For example, the mold liner 20 may be manufactured of a deformable material that may be provided in sheet form over the opening 14 of the mold cavity 10 and deformed under the molding conditions (e.g., temperature, pressure, etc.) used to form the hardenable dental material 30 into the desired shape.

Although the mold liner 20 is depicted as a unitary layer, it should be understood that it could be provided as a multilayer or other non-homogeneous structure to, e.g., provide different properties for the surface facing the hardenable dental material 30 as compared to the surface facing the interior surfaces of the mold cavity 10. Examples of some different properties that may be achieved by a multilayer structure, coating, etc. may include, but are not limited to the tensile strength of the mold liner 20, formability, durability, etc.

Also, it should be understood that the mold liner 20 itself may be treated or processed to improve its molding properties during forming of the hardenable dental material 30 in the mold cavity 10. For example, it may be desirable to preheat or heat the mold liner 20 during or just before the molding process begins to enhance its formability.

In the depicted process, the pin liner 40 is also optional, i.e., it may or may not be provided. One potential advantage of providing a pin liner 40 between the core pin 50 and the hardenable dental material 30 is that adhesion between the core pin 50 and the hardenable dental material 30 may be prevented. Another potential advantage is that the pin liner 40 may be incorporated into a package for the hardenable dental material 30 after it has been molded into the shape of the mold cavity 10.

If the pin liner 40 is not present, it may be desirable that the core pin 50 have an outer surface (i.e., the surface that contacts the hardenable dental material 30) that exhibits limited or no adhesion to the hardenable dental material 30 during the molding process. For example, the core pin 50 may be coated with, e.g., fluorinated polymers (e.g., PTFE, etc.), boron carbide, chrome, thin dense chrome, chromium nitride, electroless nickel infused with fluorinated polymers, modified tungsten disulfide (e.g., DICRONITE), etc.

The core pin 50 may be temperature controlled to assist in the molding process by, e.g., heating and/or cooling the temperature of the core pin 50. In other variations, the core pin 50 may be vented or include vacuum orifices to assist in forming the hardenable dental material 30. In some instances, ultrasonic or other vibrational energy may be supplied to the core pin 50 during the forming process.

The pin liner 40 may be constructed of a variety of different materials. For example, the pin liner 40 may be manufactured of a stretchable material that may be provided in sheet form between the core pin 50 and the hardenable dental material 30 and deformed under the molding conditions (e.g., temperature, pressure, etc.) used to form the hardenable dental material 30 into the shape of the mold cavity 10.

Stretching of the pin liner 40 may reduce the chances of unwanted voids in the molded hardenable dental article (due to, e.g., wrinkling of the pin liner 40). Furthermore, stretching of the pin liner 40 during the molding process may also enhance intimate contact between the pin liner 40 and the molded hardenable dental article.

Although the pin liner 40 is depicted as a flat sheet or film that is deformed by the core pin 50, in alternative embodiments the pin liner 40 may be preformed (partially or wholly) such that it conforms to the shape of the core pin 50. In such embodiments, the pin liner 40 may be constructed as a shell that receives the core pin 50. Although suitable materials for such pin liners may be the same as those described herein for the deformable mold liner 20, the thickness of the materials used in a preformed pin liner may be greater such that the preformed pin liner is a self-supporting structure that can maintain its shape in opposition to the force of gravity. Such preformed pin liners may also assist the hardenable dental article formed within the mold cavity to maintain its shape by supporting the hardenable dental article from within (although it may be possible that pin liners deformed by the core pin 50 during the molding process may also provide some support to assist the hardenable dental articles in maintaining their shape from within).

Although the pin liner 40 is depicted as a unitary layer, it should be understood that it could be provided as a multilayer or other non-homogeneous structure to, e.g., provide different properties for the surface facing the hardenable dental material 30 as compared to the surface facing the outer surfaces of the core pin 50. Examples of some different properties that may be achieved by a multilayer structure, coating, etc. may include, but are not limited to the tensile strength of the pin liner 40, formability, durability, control over surface energy, control over release properties, etc.

Also, it should be understood that the pin liner 40 itself may be treated or processed to improve its molding properties during forming of the hardenable dental material 30. For example, it may be desirable to preheat or heat the pin liner 40 during or just before the molding process begins to, e.g., enhance its formability.

After removing the hardenable dental material 30 and mold liner 20 from the mold cavity 10, at least a portion of the liner 20 may be retained in intimate contact with the outer surfaces of the hardenable dental article formed of the hardenable dental material 30. One example of such a construction is depicted in FIG. 2A.

Figure 2A:
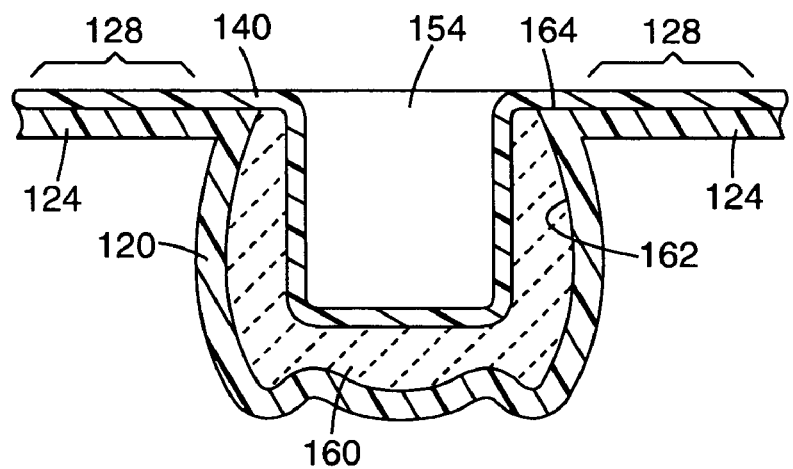
FIG. 2A is a cross-sectional view of one illustrative hardenable dental article in a package according to the present invention.

In FIG. 2A, one embodiment of a packaged, shaped hardenable dental article 160 manufactured in accordance with the present invention is depicted in a cross-sectional view. The hardenable dental article 160 includes outer surfaces 162 that are in intimate contact with package cover 120. The hardenable dental article 160 also includes a base 164 and a package base 140 located over the base 164.

The package cover 120 may include a flange 124 extending away from the hardenable dental article 160 proximate the base 164. The flange 124 may provide a convenient location at which the package base 140 may be attached to the flange 124 such that the hardenable dental article 160 is sealed within the package cover 120 and the package base 140. The seal 128 between the package cover 120 and the package base 140 may be accomplished by any suitable technique or combination of techniques, e.g., heat sealing, adhesives, cold sealing, chemical welding, ultrasonically, etc. The seal 128 may be a peelable seal, i.e., separation of the package cover 120 and the package base 140 be accomplished without significant deformation of the hardenable dental article 160 located therein.

The area of the flange 124 (or any other location on package cover 120 or package base 140) may also provide a convenient location for indicia that may be useful to identify the hardenable dental article, the hardenable dental material, a date by which the hardenable dental article should be used, etc.

With reference to the process illustrated in FIG. 1, the package cover 120 may be formed from the mold liner 20 and the package base 140 may be formed from the pin liner 40. If the hardenable dental article 160 is to be a hollowed out dental crown, then an interior cavity 154 may be formed in the base 164 of the hardenable dental article 160 as seen in FIG. 2A.

Although the package cover 120 and the package base 140 are each depicted as unitary layers, it should be understood that one or both could be provided as a multilayer or other non-homogeneous structure to, e.g., provide different properties for the surface facing the hardenable dental article 160 as compared to the surface facing away from the hardenable dental article, to provide vapor barrier properties, to provide moisture barrier properties, to provide sealing layers (e.g., heat sealable thermoplastic layers, adhesive layers, etc.).

In a variation from the process as shown in FIG. 1, the package base 140 may not be deformed as part of the process of forming the hardenable dental material. Rather, the package base 140 may be provided as a preformed article having the shape seen in FIG. 2A that is inserted into the mass of hardenable dental material (30 in FIG. 1). If it has enough structural stiffness, the package base 140 may itself function as a core pin for the molding of the hardenable dental article 160. As depicted, the package base 140 may include a void 154 as depicted in FIG. 2A that may receive a core pin shaped driver (see, e.g., core pin driver 50 in FIG. 1) during the manufacturing process. Alternatively, the package base 140 may be formed with a solid mass of material in the volume of the void 154, with that solid mass of material having sufficient strength to deform the hardenable dental material during manufacturing of the hardenable dental article 160.

If the hardenable dental article 160 is manufactured of, e.g., a photocurable material, the package cover 120 and/or package base 140 may function as an actinic light barrier to provide protection from actinic radiation that may otherwise prematurely harden the hardenable dental material forming the hardenable dental article 160. For example, the package cover 120 and/or the package base 140 may transmit less than 1% of actinic radiation incident thereon. Methods and materials of providing such light barrier properties (e.g., by pigments, etc.) are known to those skilled in the art. Examples may be described in U.S. Pat. No. 5,538,129 (Chester et al.); U.S. Pat. No. 5,552,177 (Jacobs et al.); U.S. Pat. No. 5,636,736 (Jacobs et al.); and U.S. Pat. No. 5,785,178 (Kvitrud et al.), etc.

The package cover 120 and/or package base 140 may be selected to provide a desired level of oxygen permeability to control exposure of the hardenable dental article 160 located therein to oxygen during, e.g., storage.

Figure 2B:
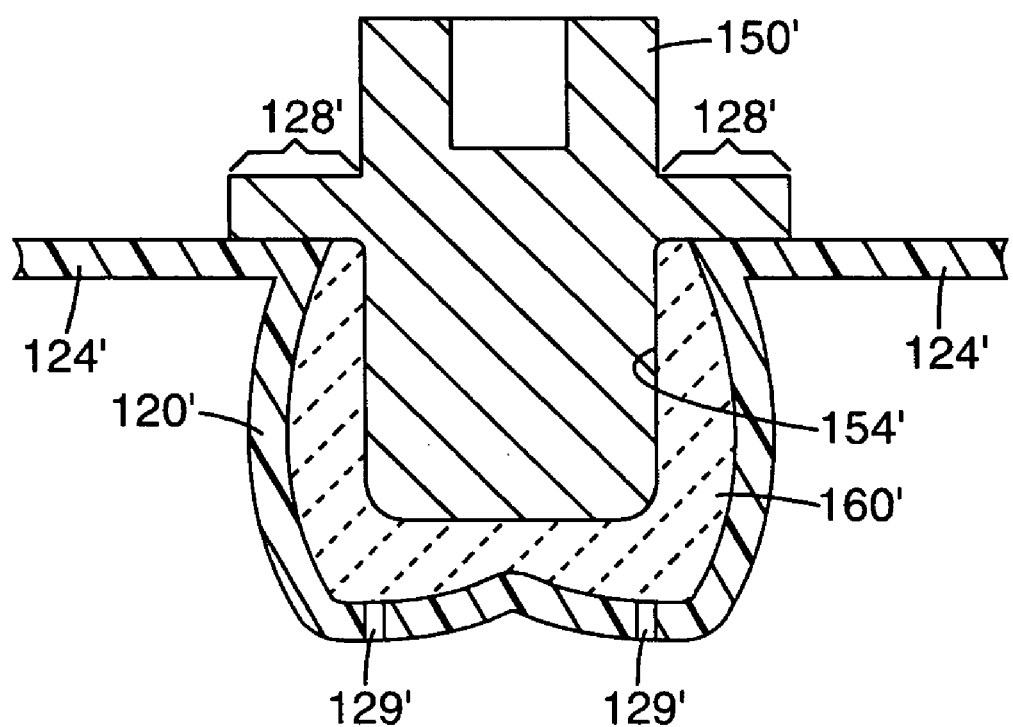
FIG. 2B is a cross-sectional view of another illustrative hardenable dental article in a package according to the present invention.

FIG. 2B depicts an alternative package construction that includes a package cover 120' in which a shaped hardenable dental article 160' is located in a manner similar to hardenable dental article 160 in package cover 120. The package also includes a solid core pin 150' that may preferably function as a package base, with the hardenable dental article 160' located within the volume defined by the package cover 120' and the core pin 150'. The core pin 150' may preferably be provided as a separate piece part attached to a driver such that the core pin 150' remains attached to the molded hardenable dental article 160'. The core pin 150' may be used, in some instances, to assist in handling of the hardenable dental article 160'.

The package cover 120' may include a flange 124' extending away from the hardenable dental article 160'. The flange 124' may provide a convenient location at which the core pin 150' may be attached to the flange 124' such that the hardenable dental article 160' is sealed within the package cover 120' and the core pin 150' which essentially functions as a package base. The seal 128' between the package cover 120' and the core pin 150' may be accomplished by any suitable technique or combination of techniques, e.g., heat sealing, adhesives, cold sealing, chemical welding, ultrasonically, etc. The seal 128' may be a peelable seal, i.e., separation of the package cover 120' and the core pin/package base 150' may be accomplished without significant deformation of the hardenable dental article 160' located therein.

Another optional feature depicted in the embodiment of FIG. 2B includes venting of the package cover 120'. The venting is provided by one or more vent holes 129' depicted in the package cover 120'. The vent holes 129' may be provided in addition to the opening into the package cover 120' through which hardenable dental material is inserted to form the hardenable dental article 160'. The vent hole or holes 129' may assist in complete filling of the package cover 120' during molding by providing a path through which air can escape from the package cover 120'. It may be preferred that the vent hole or holes 129' be small enough such that significant amounts of the hardenable dental material in the hardenable dental article 160' does not pass through the holes 129' during the filling/molding process.

Suitable materials for the mold liners, pin liners, package covers, package bases, and/or core pins will preferably be selected based on the required physical characteristics of the component in question. In other words, deformable materials may be selected for mold liners that will be deformed by the hardenable dental materials as described herein while more structurally sound, less flexible materials may be preferred for the preformed mold liners, pin liners, core pins, etc. that may be used to deform hardenable dental materials as described herein. Examples of some suitable materials may include, but are not limited to, e.g., polypropylenes, polyethylenes, polyurethanes, polyesters, polystyrenes, vinyls, thermoplastic elastomers, elastomeric films (e.g., rubber, latex, etc.), fluorinated polymers (e.g., FEP, PFA, THV, ECTFE, TEFLON, etc.), PVC, plasticized PVC, polyvinyl acetal, elastic-plastic films (e.g., blends of KRATON and polypropylene), copolymers, water soluble polymers (e.g., selected from the group consisting of polyvinylpyrrolidones, polyvinylpyrrolidone/vinyl acetate copolymers, polyvinyl alcohols, polyethylene oxides, polyacrylamides, polyacrylic acids, polysaccharides and synthetically modified polysaccharides (e.g., cellulose ether polymers), alginates (e.g., sodium alginate), polyethyl oxazolines, esters of polyethylene oxide, esters of polyethylene oxide and polypropylene oxide copolymers, urethanes of polyethylene oxide, urethanes of polyethylene oxide and polypropylene oxide copolymers, etc.). Further, the components such as the mold liner, pin liner, packages cover, package base, core pin, etc. may include one or more coatings (e.g., silicone, etc.) to enhance formability, release from the hardenable dental article, etc.

Figure 3:
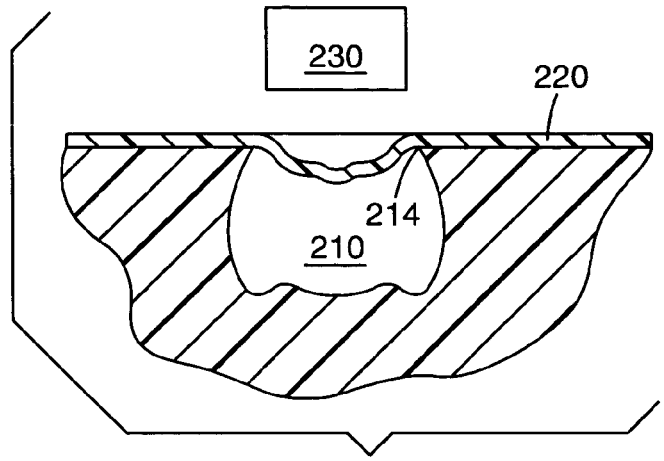
FIG. 3 is a schematic diagram of one illustrative variation in a manufacturing process according to the present invention.

FIG. 3 illustrates another variation in the manufacturing process in which a mold liner 220 is located over the opening 214 of a mold cavity 210. The depicted mold liner 220 is partially deformed before the hardenable dental material 230 is introduced into the mold cavity 210. The preforming may be accomplished by forcing the liner 220 into the mold cavity 210. Alternatively, preforming of the mold liner 220 may occur outside of the mold cavity 210. Preforming of the mold liner 220 in this manner may be accomplished with a tool (not shown) or by any other suitable technique such as fluid pressure, vacuum within the mold cavity 210, etc. It may be helpful if the mold liner 220 is heated or otherwise processed to improve its formability.

Figure 4:
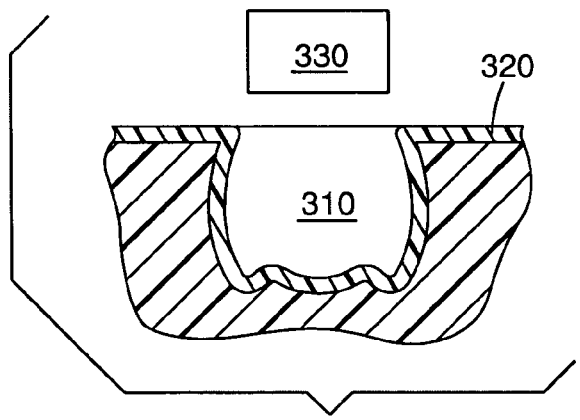
FIG. 4 is a schematic diagram of another illustrative variation in a manufacturing process according to the present invention.

FIG. 4 also illustrates another variation in the manufacturing process in which the mold liner 320 is deformed such that it replicates the shape of the mold cavity 310 before hardenable dental material 330 is introduced into the mold cavity 310. As above, preforming of the mold liner 320 in this manner may be accomplished with a tool (not shown) or by any other suitable technique such as, e.g., fluid pressure, vacuum within the mold cavity 310, etc. It may be helpful if the mold liner 320 is heated or otherwise processed to improve its formability.

Figure 5:
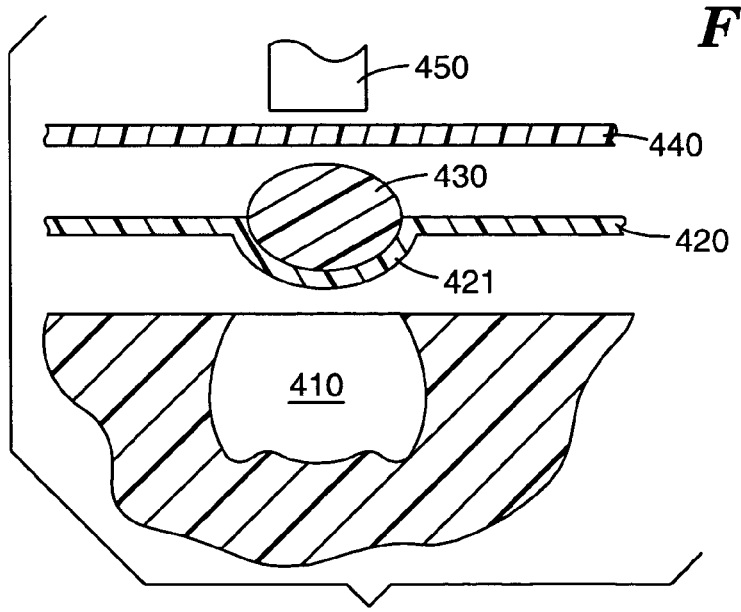
FIG. 5 is a schematic diagram of an alternative illustrative manufacturing process according to the present invention.
Figure 6:
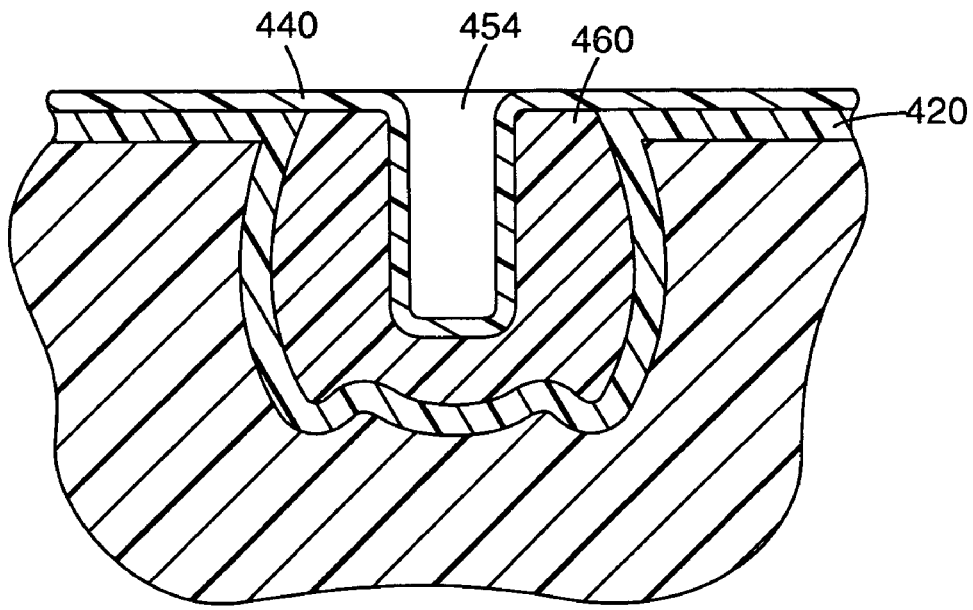
FIG. 6 is a schematic diagram of the manufacturing process of FIG. 5, with the hardenable dental material located within the mold cavity.

FIGS. 5 & 6 depict another manufacturing process in which the hardenable dental material 430 is located within a pocket 421 formed in mold liner 420 before the mold liner 420 and hardenable dental material 430 are introduced into the mold cavity 410. As seen in FIG. 5, the process includes an optional pin liner 440 located between the hardenable dental material 430 and the core pin 450. FIG. 6 depicts the hardenable dental material formed into the shape of a hardenable dental article 460 within cavity 410, including a void 454 formed by the core pin 450.

The pocket 421 in mold liner 420 may be formed under conditions of pressure, temperature, etc. using the hardenable dental material 430 itself. For example, upstream of the portion of the manufacturing process depicted in FIG. 5, the hardenable dental material 430 may be forced against the mold liner 420 under conditions of temperature, pressure, etc. such that the portion of the mold liner 420 forming the pocket 421 is permanently or plastically deformed. Alternatively, the mold liner 420 itself may be deformed by, e.g., vacuum forming, blow molding, cold forming/embossing, thermoforming, injection molding, compression molding, etc., such that the pocket 421 is formed before the hardenable dental material 430 is placed therein.

The mold liner 420 and pin liner 440 may be retained in intimate contact with the hardenable dental article 460 and attached together to form a package containing the hardenable dental article 460 after removal from the mold cavity 410 if so desired (and as described with respect to other embodiments elsewhere herein).

Figure 7:
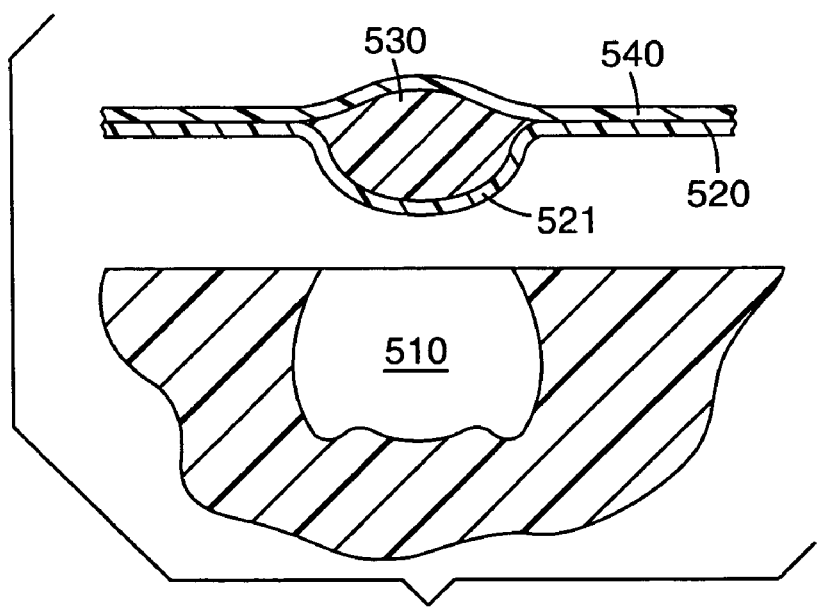
FIG. 7 is a schematic diagram of still another alternative illustrative manufacturing process according to the present invention.

FIG. 7 depicts still another alternative manufacturing process according to the present invention in which the hardenable dental material 530 is located within a volume defined by a mold liner 520 and a pin liner 540 before the hardenable dental material 530 and the mold liner 520 are introduced into the mold cavity 510. In this embodiment, the mass of hardenable dental material 530 may also be sealed within the mold liner 520 and pin liner 540 before forming. For example, the mold liner 520 and pin liner 540 may be adhered together, heat sealed, cold sealed, chemically welded, ultrasonically welded, etc. to enclose the hardenable dental material.

As discussed with respect to FIGS. 5 & 6, the hardenable dental material 530 may be located within a pocket 521 formed in the mold liner 520. Alternatively, however, the pin liner 540 may be used to form a pocket in addition to or in place of the pocket 521 formed in the mold liner.

Figure 8A:
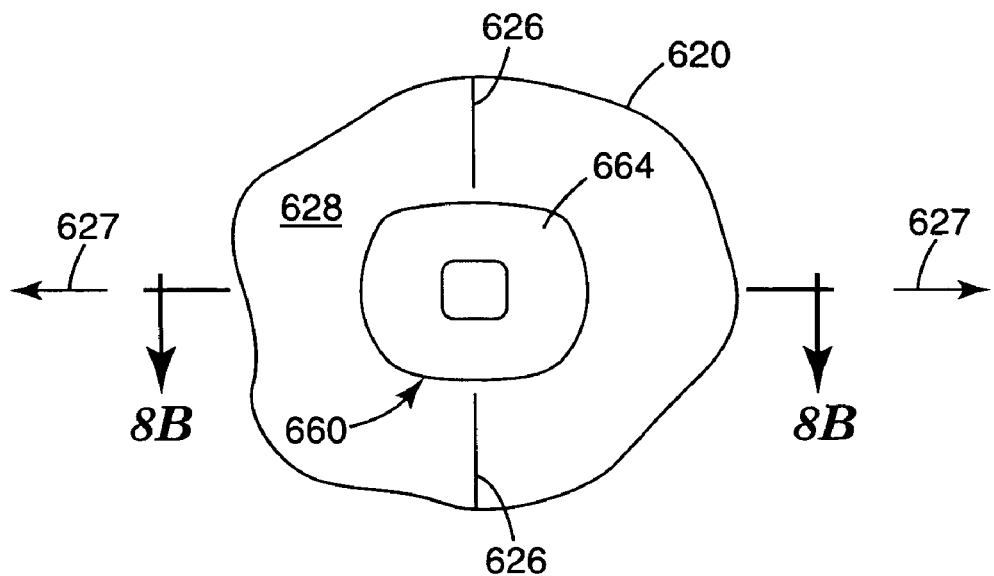
FIG. 8A is a plan view of the base of one illustrative hardenable dental article in a package in accordance with the present invention.
Figure 8B:
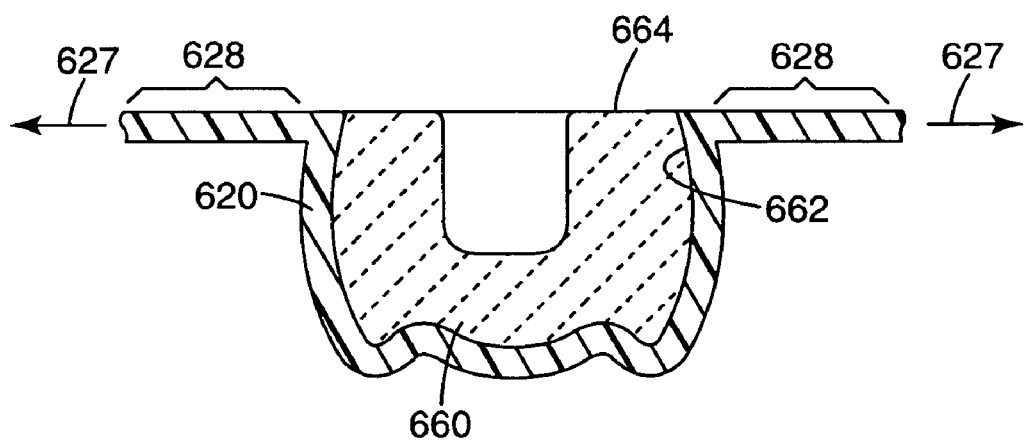
FIG. 8B is a cross-sectional view of the hardenable dental article of FIG. 8A taken along line 8B-8B in FIG. 8A.

FIG. 8A is a plan view of the base 664 of a hardenable dental article 660 located within an outer liner 620 and FIG. 8B is a cross-sectional view of the hardenable dental article 660 and outer liner 620 taken along line 8B-8B in FIG. 8A. The outer liner 620 is preferably in intimate contact with the outer surfaces 662 of the hardenable dental article 660. The hardenable dental article 660 and outer liner 620 depicted in FIGS. 8A & 8B may be manufactured using the methods described herein.

The depicted outer liner 620 includes a flange portion 628 extending away from the hardenable dental article 660. The outer liner 620 may be a stretchable film or other structure such that deforming (e.g., stretching, tearing, etc.) the outer liner 620 causes it to release from the outer surfaces 662 of the hardenable dental article 660 with little or no deformation of the shape of the hardenable dental article 660. As such, the outer liner 620 may function as a sacrificial mold body in accordance with the present invention. To improve the release characteristics, it may be desirable to provide one or more slits 626 in the flange portion 628 of the outer liner 620 and grasp the flange portions 628 to stretch the outer liner 620 in the directions of arrows 627 and/or tear it along the slits 626. If the outer liner 620 is made of a water soluble polymer, removal of the hardenable dental article 660 may be facilitated by contacting the outer liner 620 with water (by, e.g., spraying, immersion in a water bath, etc.).

Figure 9A:
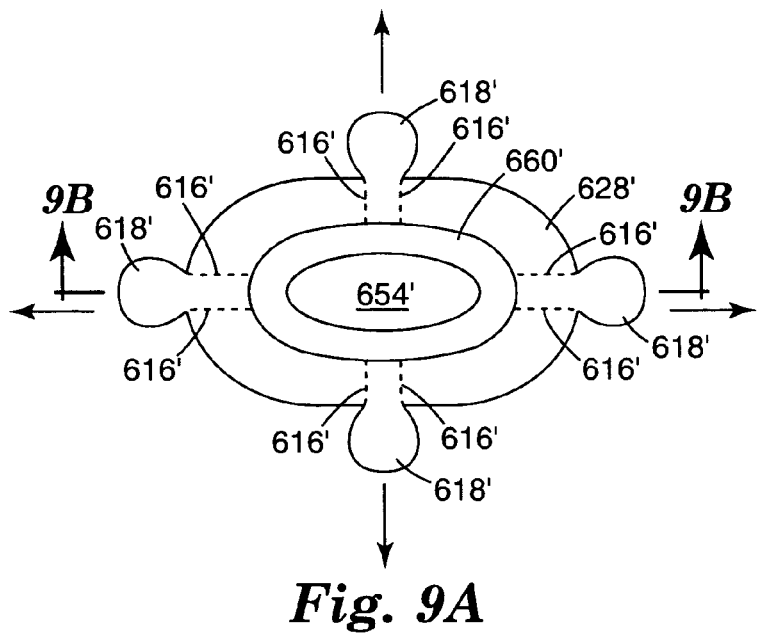
FIG. 9A is a plan view of the base of another illustrative hardenable dental article in a package in accordance with the present invention.
Figure 9B:
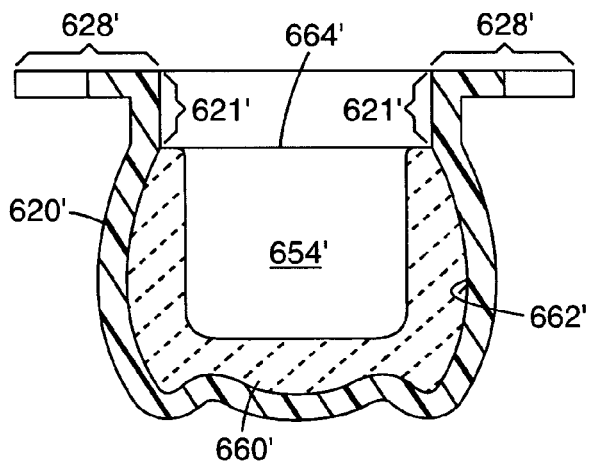
FIG. 9B is a cross-sectional view of the hardenable dental article of FIG. 9A taken along line 9B-9B in FIG. 9A.
Figure 9C:
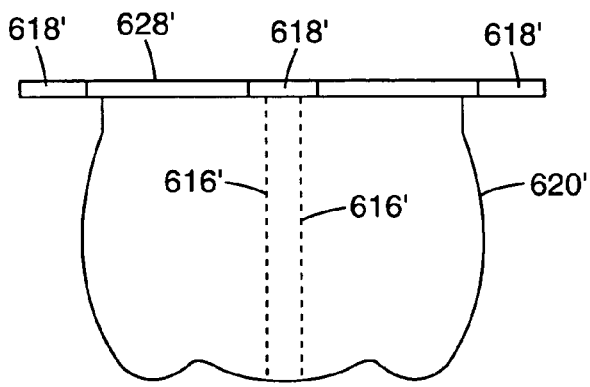
FIG. 9C is a side elevational view of the packaged article of FIGS. 9A & 9B.

FIGS. 9A-9C depict another embodiment of the invention in which a hardenable dental article 660' is located within an outer liner 620' that may function as a sacrificial mold body in accordance with the present invention. The outer liner 620' is preferably in intimate contact with the outer surfaces 662' of the hardenable dental article 660'. The hardenable dental article 660' and outer liner 620' depicted in FIGS. 9A-9C may be manufactured using the methods described herein.

The depicted outer liner 620' includes a flange portion 628' extending away from the hardenable dental article 660'. The outer liner 620' may be a stretchable film or other structure such that deforming (e.g., stretching, tearing, etc.) the outer liner 620' causes it to release from the outer surfaces 662' of the hardenable dental article 660' with little or no deformation of the shape of the hardenable dental article 660'.

It may be desirable to provide one or more lines of weakness 616' in the outer liner 620' to assist with the removal of the outer liner 620' from the hardenable dental article 660' located therein. The lines of weakness 616' may take a variety of forms, e.g., lines of perforations, thinned lines in which the wall thickness of the outer liner 620' is reduced relative to the surrounding wall thickness, score lines formed after the outer liner 620' is manufactured, etc. In yet another variation, each line of weakness may be defined by a filament in the outer liner 620' such that the liner preferentially separates along the filament. Other variations of providing a means of separation for an outer liner may be envisioned by those skilled in the art.

The lines of weakness 616' may preferably extend onto the flange portion 628' of the outer liner 620'. The flange 628' may also include one or more tabs 618' that can be grasped. Movement of tabs 618' outward from the hardenable dental article 660' may preferably cause the outer liner 620' to separate along the lines of weakness 616'.

It may be preferred that the lines of weakness 616' be provided in pairs of generally parallel lines of weakness 616'. It may further be preferred that one of the tabs 618' be located between one or more of the pairs of generally parallel lines of weakness 616'. Removal of the outer liner 620' from the hardenable dental article 660' may be facilitated because the portion of the outer liner 620' located between a pair of generally parallel lines of weakness can typically be peeled away from the hardenable dental article 660' without placing significant stress on the hardenable dental article 660' that could otherwise deform the hardenable dental article 660'. After the strips have been removed, the remainder of the outer liner 620' can typically be easily removed from the hardenable dental article 660'. Although the outer liner 620' includes four pairs of generally parallel lines of weakness 616', outer liners according to the present invention may be provided with any selected number of pairs of lines of weakness.

Another optional feature of the present invention that is depicted in FIGS. 9A-9C is the underfilling of the cavity formed within the outer liner 620'. As seen in FIG. 9B, the hardenable dental article 660', which includes an interior cavity 654' and a base 664', does not occupy the entire volume of the outer liner 620'. Rather, portions of the interior surfaces proximate the opening into the cavity are substantially free of any hardenable dental material, such that an unfilled margin 621' is provided between the hardenable dental article 660' and the opening. The unfilled margin may provide potential advantages during removal of the outer liner 620' because tearing or other deformation of the outer liner 620' to facilitate removal may be initiated within the area of the unfilled margin 621'. As a result, the forces transmitted to the hardenable dental article 660' (forces that could distort the shape of the hardenable dental article 660') may be significantly reduced or eliminated.

Figure 10:
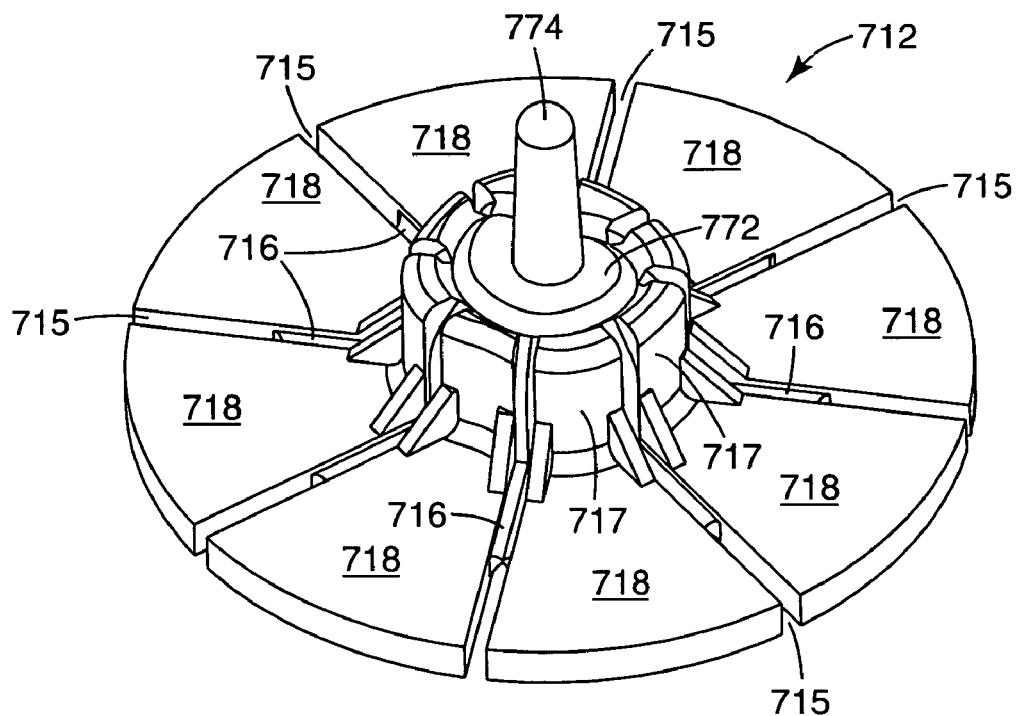
FIG. 10 is a perspective view of the outer surface of one illustrative sacrificial mold cavity/body used in connection with the present invention.
Figure 11:
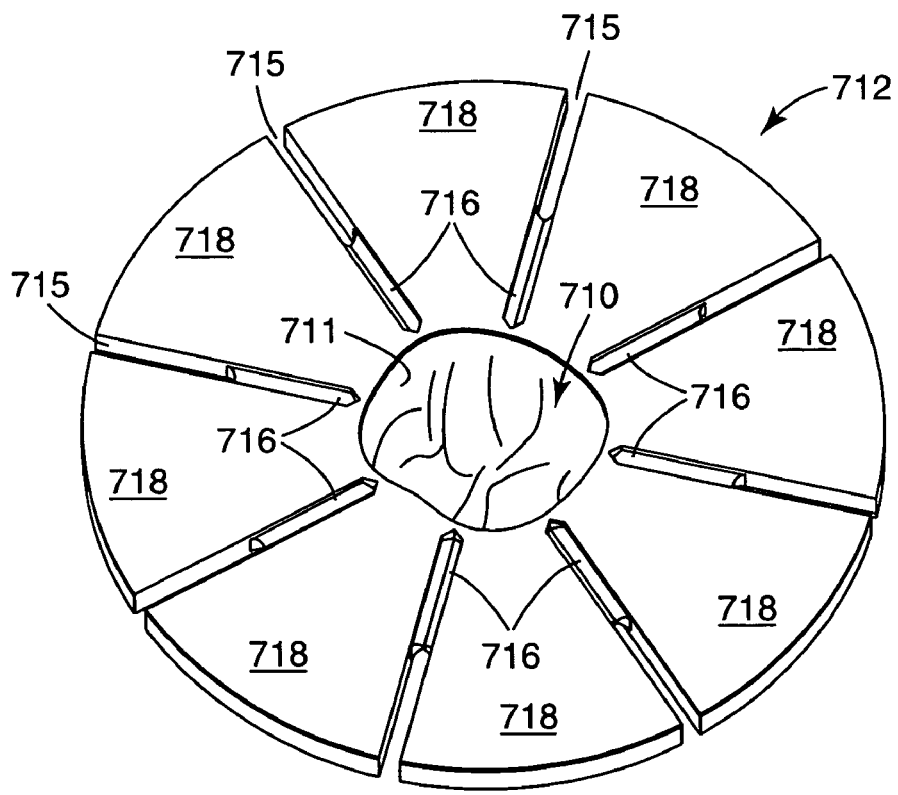
FIG. 11 is a perspective view of the opposite side of the sacrificial mold of FIG. 10 depicting the mold cavity formed therein.

FIGS. 10 & 11 are perspective views, respectively, of the outer and base surfaces of one exemplary embodiment of another sacrificial mold cavity that may be used to manufacture and, potentially, package a hardenable dental article according to the present invention. The sacrificial mold cavity 710 is formed in a sacrificial mold body 712 that may include one or more lines of weakness 716 formed therein, wherein the lines of weakness define sections 717 in the sacrificial mold body 712.

The interior surfaces 711 of the sacrificial mold cavity 710 (see FIG. 11) are in the shape of the desired hardenable dental article such that when hardenable dental material is forced into the sacrificial mold cavity 710, it takes the shape of the desired hardenable dental article in the sacrificial mold cavity 710 itself.

The lines of weakness 716 may define lines along which the sacrificial mold body 712 may separate when tension is applied across the line of weakness 716 or when a shearing force is generated on opposite sides of the line of weakness 716. The lines of weakness 716 may take a variety of forms, e.g., thinned lines in which the wall thickness of the mold body 712 is reduced relative to the surrounding wall thickness, score lines formed after the mold body 712 is manufactured, etc. In yet another variation, each line of weakness 716 may be defined by a filament molded in the body 712 such that the body preferentially separates along the filament. Other variations of providing a means of separation for a sacrificial mold cavity may be envisioned by those skilled in the art.

Lines of weakness may be provided in any desired orientation on the sacrificial mold body 712 (i.e., the depicted lines of weakness 716 are not to be construed as limiting the orientation of lines of weakness used in connection with the invention). For example, for a sacrificial mold cavity 710 forming a dental crown, lines of weakness that extend around the sacrificial mold body 712 in helical spirals from the portion of the mold cavity 712 forming the margin to the incisal/occlusal surfaces of the dental crown may alternatively be provided. Other variations in the orientation or paths of lines of weakness used in connection with sacrificial mold cavities of the present invention may also be provided.

The mold body 712 may also include a flange or tab 718 associated with one or more of the mold sections 717. The tabs 718 may be used to facilitate handling of the mold body 712, to provide a location on which a package base may be attached to seal the sacrificial mold cavity 710 after locating the hardenable dental material therein, and/or to provide a location at which the mold body 712 may be grasped to apply the force required to separate the one or more lines of weakness 716 in the mold body 712.

The flanges 718 (or any other location on the mold body 712) may also provide a convenient location for indicia that may be useful to identify the hardenable dental article, the hardenable dental material, a date by which the hardenable dental article should be used, etc.

Separation of the sacrificial mold body 712 along the one or more lines of weakness 716 may be facilitated by a variety of optional features. For example, notches 715 may be provided at the ends of the lines of weakness 716. The notches 715 may act as stress concentrators to initiate separation along the lines of weakness 716. In the depicted embodiment, the notches 715 are formed in between adjacent tabs 718, with the notches 715 transitioning into thinned lines of weakness 716.

Figure 12:
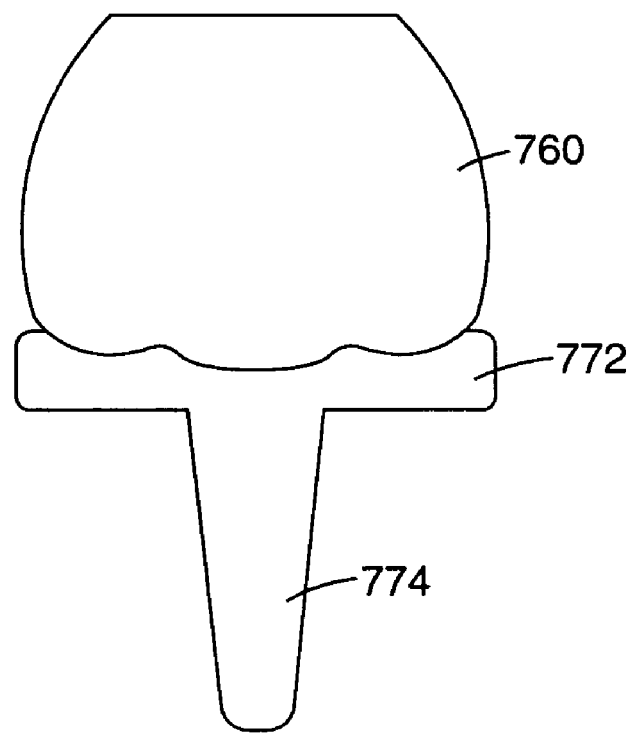
FIG. 12 is a side elevational view of an illustrative hardenable dental article on a base of the sacrificial mold body of FIG. 10 after removal of the mold sections.

Another optional feature depicted in connection with the sacrificial mold body 712 is a base line of weakness that extends about the periphery of the mold body 712 proximate, e.g., the incisal/occlusal surfaces formed by the mold cavity 710. As each section 717 is separated from its adjacent section or sections 717 (in a process similar to, e.g., peeling petals from flower), the sections may be separated completely from the mold body 712 along base line of weakness. After all of the sections 717 are removed, the base line of weakness may preferably define a base 772 that may remain attached to the hardenable dental article 760 as seen in FIG. 12. A post or stud 774 attached to the base 772 as depicted may facilitate handling of the hardenable dental article 760.

The mold body 712 may be manufactured of any suitable material or materials that may be provided in the desired shape and that will function to form or shape the hardenable dental material used to form the hardenable dental article 760. Examples of suitable materials for the mold body 712 may include, but are not limited to, thermoplastic polymers, thermoplastic elastomers, polyethylenes, polypropylenes, polystyrenes, polyesters (e.g., poly(ethylene terephthalate)), etc.

A number of approaches may be employed to facilitate release of the interior surface 711 of the sacrificial mold cavity 710 from the hardenable dental material used to form the hardenable dental article 760. For example, additives may be provided in the material used to form the mold body. Examples of some suitable additives may include, but are not limited to, fluoropolymers, graphite, fatty acids, low molecular weight polyethylene, silicone, hydrocarbon waxes, metallic stearates, etc. In another example, the interior surfaces 711 of the sacrificial mold cavity 710 may include a coating formed thereon to enhance release from the hardenable dental material, e.g., silicone, fluorinated polymers, etc.

In still another approach, a mold liner (as described above with respect to FIGS. 1 and 3-7) may be used in connection with the sacrificial mold cavity 710. If a mold liner is used, it may be retained in intimate contact with the outer surfaces of the hardenable dental article after removal of the mold body 712.

Furthermore, if no mold liner is used in connection with sacrificial mold cavity 710, it is preferred that the lines of weakness 716 do not include any voids, perforations, or other structures that could fill with the hardenable dental material during the molding process because such features would change the shape of the hardenable dental article 760 thus formed. For example, it may be preferred that, on the interior surfaces 711 of the sacrificial mold cavity 710, the lines of weakness 716 be indistinguishable from the remainder of the interior surfaces 711 of the sacrificial mold cavity 710. If, however, a mold liner is used, then the lines of weakness 716 may include voids (e.g., lines of perforations formed in the mold body 712) because such perforations could be sealed by the mold liner. Furthermore, such perforations may act to vent the sacrificial mold cavity 710.

Although the exemplary embodiment of a sacrificial mold cavity of FIGS. 10-12 includes lines of weakness formed therein, other sacrificial mold cavities used in connection with hardenable dental articles of the present invention may not include lines of weakness to assist in removal of the hardenable dental articles. For example, another sacrificial mold cavity may be made of, e.g., an elastomeric material (e.g., rubber, thermoplastic elastomers, etc.) or a material exhibiting a low tear strength.

The internal surfaces of a sacrificial mold cavity may have the shape of the hardenable dental article while the external surfaces of the sacrificial mold body in which the mold cavity is located may conform to the shape of the hardenable dental article located within the cavity. One example of such a sacrificial mold body and cavity is depicted in, e.g., FIG. 2A in the form of the package cover 120.

Alternatively, the exterior shape of a sacrificial mold cavity may not conform to the shape of the hardenable dental article located within the mold cavity. For example, the exterior shape of the sacrificial mold cavity may be a generic shape such as, for example, a block, cylinder, etc.

If any sacrificial mold body used in connection with the present invention does not, itself, possess sufficient strength to mold or form the hardenable dental material, then the sacrificial mold body (and the mold cavity it contains) may be supported by a support structure during the molding process. One example of a suitable support structure may be, e.g., the mold cavity 10 depicted in connection with FIG. 1 and described as one example of a structure used to form the package cover 120 of FIG. 2A.

Typically, the support structure will preferably conform to the exterior shape of the sacrificial mold body in which the sacrificial mold cavity is located. As a result, if the exterior shape of the sacrificial mold body (such as package cover/mold body 120 of FIG. 2A) conforms to the shape of the hardenable dental article, then the support structure used to support the mold body will include interior surfaces that also conform to the exterior shape of the sacrificial mold body. If the exterior shape of the sacrificial mold body is generic, i.e., in the shape of a cylinder, block, etc., then the support structure used to support the mold body will typically include interior surfaces that conform to the generic shape of the sacrificial mold body.

Figure 13:
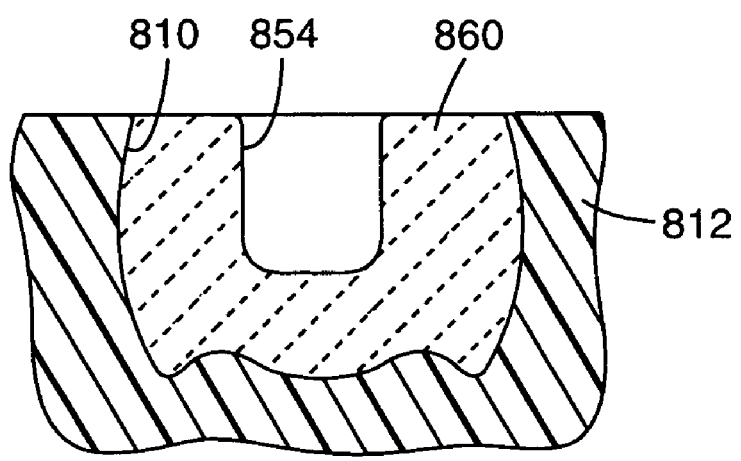
FIG. 13 is a cross-sectional view of another illustrative sacrificial mold cavity according to the present invention.

One illustrative example of a sacrificial mold cavity having a generic outer shape and an inner cavity in the shape of a desired hardenable dental article is depicted in FIG. 13, where mold body 812 defines a mold cavity with inner surfaces 810. A hardenable dental article 860 is formed within the mold cavity defined by inner surfaces 810. The hardenable dental article 860 may include an inner cavity 854.

The mold body 812 may be formed of, e.g., elastomeric materials and/or materials exhibiting low tear strength to facilitate removal of the hardenable dental article 860 as discussed above. Alternatively, the mold body may be formed of soluble polymers (e.g., water soluble polymers selected from the group consisting of polyvinylpyrrolidones, polyvinylpyrrolidone/vinyl acetate copolymers, polyvinyl alcohols, polyethylene oxides, polyacrylamides, polyacrylic acids, polysaccharides and synthetically modified polysaccharides (e.g., cellulose ether polymers), alginates (e.g., sodium alginate), polyethyl oxazolines, esters of polyethylene oxide, esters of polyethylene oxide and polypropylene oxide copolymers, urethanes of polyethylene oxide, urethanes of polyethylene oxide and polypropylene oxide copolymers, etc.). The hardenable dental article 860 could be removed from the sacrificial mold body 812 at some point after the forming operation either by softening and/or dissolving the soluble mold body 812 through contact with an appropriate solvent (e.g., a water bath or spray for water soluble polymers).

As used herein and in the appended claims, the singular forms "a," "and," and "the" include plural referents unless the context clearly dictates otherwise.

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of manufacturing a hardenable dental article, the method comprising:
   providing a mold cavity in a shape of a hardenable dental article, wherein the mold cavity comprises an opening;
   forcing a hardenable dental material into the mold cavity through the opening;
   providing an outer liner between the hardenable dental material and the mold cavity, wherein the outer liner is a deformable material provided in sheet form; and
   removing the hardenable dental material and the outer liner from the mold cavity, wherein the hardenable dental material has the shape of the hardenable dental article and the outer liner sheet releases from the hardenable dental article after or during removal from the mold cavity.

2. A method according to claim 1, further comprising locating the outer liner over the opening of the mold cavity, wherein forcing the hardenable dental material into the mold cavity comprises simultaneously forcing the outer liner into the mold cavity, wherein both the outer liner and the hardenable dental material take the shape of the hardenable dental article.

3. A method according to claim 1, further comprising:
locating the outer liner over the opening of the mold cavity; and
forcing the outer liner into the mold cavity before forcing the hardenable dental material into the mold cavity.

4. A method according to claim 3, wherein forcing the outer liner into the mold cavity comprises only partially replicating the mold cavity with the outer liner.

5. A method according to claim 4, wherein forcing the hardenable dental material into the mold cavity further forces the outer liner into the mold cavity, wherein both the outer liner and the hardenable dental material take the shape of the hardenable dental article.

6. A method according to claim 3, wherein forcing the outer liner into the mold cavity comprises replicating the mold cavity with the outer liner, wherein the outer liner takes the shape of the hardenable dental article before forcing the hardenable dental material into the mold cavity.

7. A method according to claim 1, wherein providing the outer liner between the hardenable dental material and the mold cavity comprises:
deforming the outer liner to form a pocket therein; and
locating the hardenable dental material within the pocket in the outer liner before forcing the hardenable dental material into the mold cavity.

8. A method according to claim 1, wherein providing the outer liner between the hardenable dental material and the mold cavity comprises deforming the outer liner to form a pocket therein by forcing the hardenable dental material into contact with the outer liner, wherein the hardenable dental material is located within the pocket before forcing the hardenable dental material into the mold cavity.

9. A method according to claim 1, wherein the outer liner comprises one or more vent holes located therein.

10. A method according to claim 1, wherein the hardenable dental material fills only a portion of the mold cavity such that a portion of the outer liner comprises an unfilled margin proximate the opening of the mold cavity.

11. A method according to claim 1, wherein forcing the hardenable dental material through the opening comprises forcing a core pin against the hardenable dental material, and wherein the core pin remains embedded in the hardenable dental material after removing the hardenable dental material and the outer liner from the mold cavity.

12. A method according to claim 11, wherein the core pin forms an interior cavity within the hardenable dental article, and wherein the core pin fills the interior cavity.

13. A method according to claim 12, wherein the core pin comprises a core pin cavity within the interior cavity of the hardenable dental article.

14. A method according to claim 11, further comprising attaching the core pin to the outer liner proximate the opening of the mold cavity, wherein the hardenable dental article is enclosed by the outer liner and the core pin.

15. A method according to claim 1, wherein forcing the hardenable dental material through the opening comprises forcing a core pin against the hardenable dental material, and wherein the method further comprises providing a pin liner between the hardenable dental material and the core pin.

16. A method according to claim 15, wherein the core pin forms an interior cavity within the hardenable dental article, and wherein the pin liner lines the interior cavity.

17. A method according to claim 15, wherein the core pin forms an interior cavity within the hardenable dental article, and wherein the core pin permanently deforms the pin liner when forming the interior cavity of the hardenable dental article.

18. A method according to claim 15, wherein the core pin forms an interior cavity within the hardenable dental article, and wherein the pin liner conforms to the shape of the core pin before the core pin forms the interior cavity of the hardenable dental article.

19. A method according to claim 15, further comprising attaching the pin liner to the outer liner such that the hardenable dental article is enclosed by the outer liner and the pin liner.

20. A method according to claim 1, wherein at least a portion of the outer liner is retained on the surface of the hardenable dental article after removing the hardenable dental article from the mold cavity.

21. A method according to claim 20, wherein the method comprises removing the hardenable dental article from the outer liner by deforming the outer liner.

22. A method according to claim 1, wherein the outer liner comprises a water soluble polymer.

23. A method according to claim 22, wherein at least a portion of the outer liner is retained on the surface of the hardenable dental article after removing the hardenable dental article from the mold cavity, and further wherein the method comprises removing the hardenable dental article from the outer liner by contacting the outer liner with water.

24. A method according to claim 1, wherein the hardenable dental article comprises a hardenable dental crown.

25. The method according to claim 1 wherein the liner is retained on the outer surface of the hardneable dental article during removal from the mold cavity.

26. The method according to claim 25 wherein the liner functions as a protective barrier for the outer surfaces of the hardenable dental article.

* * * * *

UNITED STATES PATENT AND TRADEMARK OFFICE
CERTIFICATE OF CORRECTION

PATENT NO. : 7,811,486 B2  
APPLICATION NO. : 10/921648  
DATED : October 12, 2010  
INVENTOR(S) : Naimul Karim Page 1 of 1

It is certified that error appears in the above-identified patent and that said Letters Patent is hereby corrected as shown below:

Title Page 3 - Column 2 (Other Publications)
Line 14, Delete "Alslo," and insert -- Alsip, --, therefor.
Line 21, Delete "Derivitized" and insert -- Derivatized --, therefor.
Line 24, Delete "provisona" and insert -- provisional --, therefor.
Line 34, Delete "Light-gured" and insert -- Light-cured --, therefor.

Column 18
Line 47, In Claim 25, Delete "hardneable" and insert -- hardenable --, therefor.

Signed and Sealed this
Twenty-second Day of February, 2011

David J. Kappos
*Director of the United States Patent and Trademark Office*